(12) United States Patent
Miller (10) Patent No.: US 8,786,575 B2
(45) Date of Patent: Jul. 22, 2014

(54) TOUCH-SENSITIVE DEVICE AND METHOD (75) Inventor: Seth Adrian Miller, Englewood, CO (US)

(73) Assignee: Empire Technology Development LLP, Wilmington, DE (US)

( * ) Notice: Subject to any disclaimer, the term of this patent is extended or adjusted under 35 U.S.C. 154(b) by 962 days.

(21) Appl. No.: 12/467,943

(22) Filed: May 18, 2009

(65) Prior Publication Data

US 2010/0289772 A1 Nov. 18, 2010

(51) Int. Cl.
*G06K 9/00* (2006.01)
*A61B 5/00* (2006.01)
*A61B 5/145* (2006.01)

(52) U.S. Cl.
USPC ............ 345/175; 345/173; 600/549; 382/116

(58) Field of Classification Search
USPC ................. 345/175, 173; 600/549; 382/116
See application file for complete search history.

(56) References Cited

U.S. PATENT DOCUMENTS

| | | | |
|---|---|---|---|
| 4,759,369 A | 7/1988 | Taylor | |
| 5,007,423 A | 4/1991 | Branstetter et al. | |
| 5,069,214 A | 12/1991 | Samaras et al. | |
| 5,719,950 A | 2/1998 | Osten et al. | |
| 6,327,376 B1 | 12/2001 | Harkin | |
| 6,337,918 B1 * | 1/2002 | Holehan | 382/124 |
| 6,526,315 B1 | 2/2003 | Inagawa et al. | |
| 6,560,352 B2 | 5/2003 | Rowe et al. | 382/115 |
| 6,707,257 B2 | 3/2004 | Norris | |
| 7,179,230 B2 | 2/2007 | Kawatahara | |
| 2004/0252867 A1 * | 12/2004 | Lan et al. | 382/124 |
| 2005/0209515 A1 | 9/2005 | Hockersmith et al. | |
| 2006/0020216 A1 | 1/2006 | Oishi et al. | |
| 2007/0088207 A1 | 4/2007 | Mannheimer et al. | |
| 2007/0106172 A1 * | 5/2007 | Abreu | 600/549 |
| 2007/0123762 A1 | 5/2007 | Crawford et al. | |
| 2007/0179358 A1 * | 8/2007 | Perez | 600/300 |
| 2007/0183633 A1 * | 8/2007 | Hoffmann | 382/116 |
| 2007/0225581 A1 | 9/2007 | Diab et al. | |
| 2007/0244383 A1 * | 10/2007 | Talbot et al. | 600/365 |
| 2007/0265513 A1 | 11/2007 | Schenkman et al. | |

(Continued)

FOREIGN PATENT DOCUMENTS

JP 7-323162 12/1995
JP 10-108844 4/1998

(Continued)

OTHER PUBLICATIONS

J.W. Severinghaus, The Current Status of Transcutaneous Blood Gas Analysis and Monitoring, Published 1998 by Blood Gas News.*

(Continued)

*Primary Examiner* — William Boddie
*Assistant Examiner* — Michael J Eurice
(74) *Attorney, Agent, or Firm* — Dorsey & Whitney LLP (57) ABSTRACT

Techniques are generally described for touch-sensitive devices with biometric information determination capabilities. The touch-sensitive device may include one or more of a transmitter, a receiver, and a processor. The transmitter may be configured to emit light towards a surface of the touch-sensitive device and the receiver may be configured to receive reflected light from a touch to the touch-sensitive device. The processor may be arranged to receive signals from the receiver and determines biometric information, and in some examples location of touch, based on the signals.

22 Claims, 7 Drawing Sheets

(56) References Cited

U.S. PATENT DOCUMENTS

| | | | |
|---|---|---|---|
| 2007/0299322 A1 | 12/2007 | Miyajima et al. | |
| 2008/0009689 A1 | 1/2008 | Benaron et al. | |
| 2008/0082004 A1 | 4/2008 | Banet et al. | |
| 2008/0267456 A1 | 10/2008 | Anderson | |
| 2008/0285813 A1* | 11/2008 | Holm | 382/115 |
| 2008/0317302 A1 | 12/2008 | Abdallah et al. | |
| 2009/0054751 A1 | 2/2009 | Babashan et al. | |

FOREIGN PATENT DOCUMENTS

| | | |
|---|---|---|
| JP | 2005-013597 A | 1/2005 |
| JP | 2006-320549 A | 11/2006 |
| JP | 2008-130024 | 6/2008 |
| JP | 2008-242542 | 10/2008 |
| WO | WO-99/28701 | 6/1999 |
| WO | WO-01/84482 | 11/2001 |
| WO | WO-02/17778 | 3/2002 |
| WO | WO-2004/066194 | 8/2004 |

OTHER PUBLICATIONS

International Preliminary Report on Patentability in International Application No. PCT/US2010/029703 mailed on Oct. 13, 2011.
International Search Report mailed Nov. 12, 2010 for Application No. PCT/US2010/029703.
Barclay MD, Laurie, "Pluse Carbon Monoxide Oximeter Screening May be Safe, Feasible", Medscape Medical News, Feb. 22, 2008; http://www.medscape.com/viewarticle.570531.
Creaghbrown, "How does Pulse Oximetry Work?", http://www.creaghbrown.co.uk/anae/pulsox.htm.
Masimo, "Masimo Rainbow SET Pulse CO-Oximetry", http://www.masimo.com/rainbow/about.htm.
"International Search Report and Written Opinion dated Jul. 9, 2010 in regards to application PCT/US2010/034691".
"International Preliminary Report on Patentability dated Dec. 1, 2011 in regards to application PCT/US2010/034691".
EP Search Report for EP Application No. 10154700.8, mailed Apr. 17, 2013.

* cited by examiner

600 A Computer program product

610 A signal bearing medium

620 At least one of:

one or more instructions for transmitting, with a transmitter, optical energy having a first wavelength to a touch panel surface capable of receiving a touch event;
    one or more instructions for receiving, with a receiver, optical energy at the first wavelength upon occurrence of a touch event;
    one or more instructions for transmitting the received optical energy to a processor; and
    one or more instructions for determining, with the processor, biometric information based on the received optical energy.

| 622 a computer-readable medium | 624 a recordable medium | 626 a communication medium |
|---|---|---|

TOUCH-SENSITIVE DEVICE AND METHOD

BACKGROUND

Touch screens are widely used for inputting data in a variety of electronic devices including hand-held devices such as mobile phones and cameras. In prior art touch screen applications, a touch screen sensor panel is disposed over or under a display and the sensor panel is used predominately for indicating a touch, possibly the location of the touch, and/or the force of the touch. Higher level functionality is not typically tied to the touch screen device.

BRIEF DESCRIPTION OF THE FIGURES

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope. The disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are explicitly contemplated herein.

This disclosure is drawn to methods, systems, apparatuses, and computer programs related to gathering biometric information from a touch sensitive sensor. In some implementations, the touch sensor may be incorporated into a touch sensitive device, a touch screen device, or other system. The touch sensitive device may be provided with near infrared or other spectroscopy components to facilitate capturing of biometric data. Generally, any suitable type of touch sensitive device and any type of spectroscopy device may be used. Such system, including touch sensitive and spectroscopy devices, may be used with computers, terminals, mobile phones, digital appliances such as personal digital assistants (PDAs), satellite navigation devices, exercise equipment, security devices, or devices.

A touch screen is a display which may detect the presence and, in some implementations, location and/or force of a touch within a display area. The term generally refers to touch or contact to the display of the device by a finger or hand. Various touch technologies have been developed including, for example, capacitive touch, resistive touch, surface acoustic wave touch, electromagnetic touch, projected capacitance touch screens, strain gauge touch, optical imaging touch, near field imaging touch, dispersive signal technology touch, frustrated internal touch reflectance, acoustic pulse recognition touch, or other suitable touch technology. For the purposes of this description, any suitable touch screen technology may be used with a system, device, or apparatus described herein. Using various touch screen technology, a transmitter and a receiver are provided to generate optical energy and receive reflected optical energy, respectively. As used herein, touch sensitive device, touch sensitive display, touch screen, and like terms are generally intended to include all forms of touch sensitivity technology and may not include display functionality. Further, a touch event is intended to include direct contact to such touch device but may further include near contact with such touch device when supported by the touch technology.

Near infrared (NIR) spectroscopy refers to spectroscopy that uses wavelengths in the near infrared spectrum, generally from approximately 800 nm to approximately 2500 nm. NIR spectroscopy may be used to quantitatively identify levels of concentration of chemicals, such as blood analytes. NIR spectroscopy further may be used to identify changes in concentration of such chemicals among other interfering chemicals. Algorithmic processes, such as chemo metrics, may be used to separate specific molecular signatures of desired chemicals from the noise contributed by interfering compounds. While NIR spectroscopy is specifically discussed herein, it is to be appreciated that, in other implementations, mid-range spectroscopy, far range spectroscopy, or white light spectroscopy may alternatively be used.

Wavelengths in the NIR range may penetrate the human body, for example for up to several centimeters. Accordingly, NIR spectroscopy may be used as a tool for non-invasive quantitation of certain biomarkers. For example, NIR spectroscopy may be used to determine levels of blood glucose, blood alcohol, bilirubin, cholesterol, and blood oxygenation. Further, individuals may have unique spectroscopic signatures. Accordingly, NIR spectroscopy may be used as a method of biometric identification. A spectroscopic signature thus may be developed for individuals using any suitable method including, for example, that taught by U.S. Pat. No. 6,560,352. The term "biometric information" is used herein and is intended to refer to any information that may be gathered using spectroscopy including information regarding specific chemicals, information regarding biometric identification, or other information.

Accordingly, as taught herein, a transmitter and a receiver may be used to generate optical energy to determine touch to a touch sensitive device and that optical energy may further be used to derive spectroscopic information, and thereby biometric information, regarding the individual making the touch. In some examples, the described touch technology may require direct contact, generally leading to an improved signal to noise (SNR) ratio, while in other examples near contact may be sufficient without direct contact.

Figure 1:
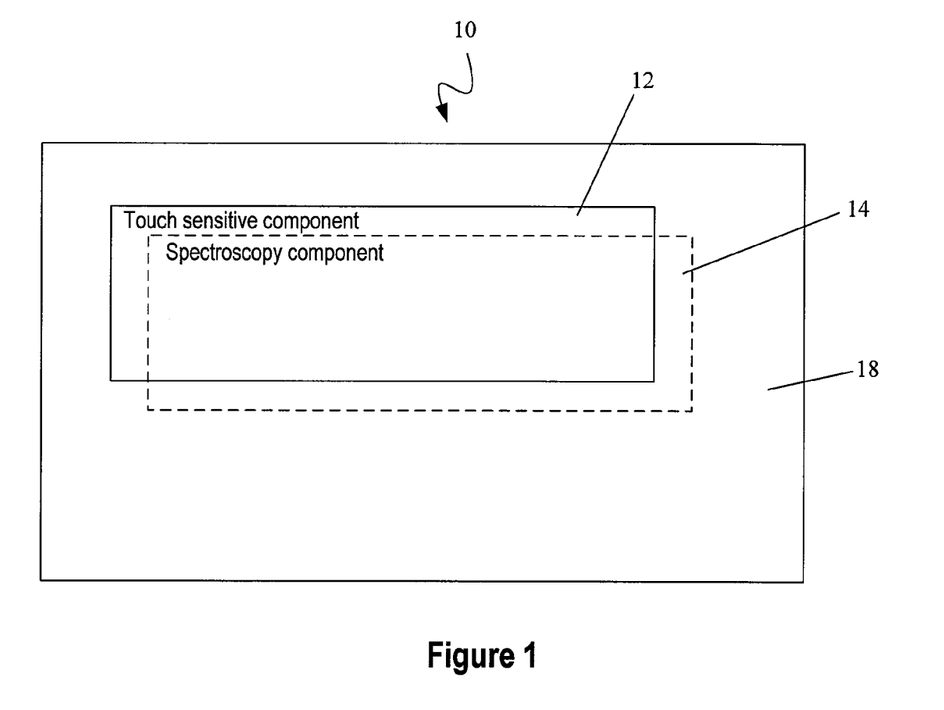
FIG. 1 depicts a touch-sensitive device having biometric information determination capabilities according to certain examples of the present disclosure.

FIG. 1 depicts a touch-sensitive device having biometric information determination capabilities according to certain examples of the present disclosure. An example system 10 may comprise a touch screen component 12 and a spectroscopy component 14, as shown in FIG. 1. The touch screen component 12 and spectroscopy component 14 may be provided as part of a further device 18. Alternatively, the touch screen component 12 and spectroscopy component 14 may form the complete system. For the purposes of illustration only, particular reference will be made to capacitive touch screen devices.

Figure 2A:
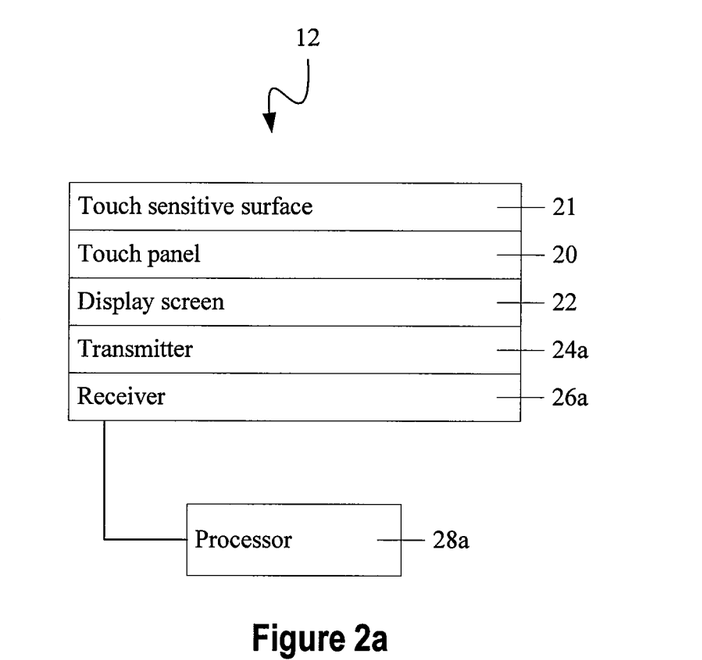
FIG. 2a depicts a touch screen component of a touch sensitive device according to certain examples of the present disclosure.

FIG. 2a depicts a touch screen component of a touch sensitive device according to certain examples of the present disclosure. As shown in FIG. 2a, the touch screen component 12 may include a touch panel 20, a touch-sensitive surface 21, a display screen 22, a transmitter 24a, a receiver (or sensor) 26a, and a processor 28a.

In some examples, the touch panel 20 may be a substantially transparent panel with a touch-sensitive surface 21. Generally, the touch panel 20 may be manufactured of a material that is both optically transparent and NIR transparent. For example, the touch panel 20 may be formed of a suitable polymer, quartz, or glass treated to enhance transparency in desired spectra. The touch panel 20 may be positioned in front of the display screen 22 so that the touch-sensitive surface 21 covers the viewable area of the display screen 22. The display screen 22 operates to display information, data, pictures, and the like to the user.

The transmitter 24a may comprise an infrared (IR) transmitter for transmitting IR radiation. Correspondingly, the receiver 26a may comprise an IR receiver for receiving IR radiation reflected by a finger or other object in proximity to the panel. The transmitter and receiver may alternatively be configured for transmitting and receiving, respectively, near-infrared or other radiation but, for the sake of simplicity, reference will be made to NIR herein. Generally, the type of receiver is selected to match the corresponding type of transmitter.

The transmitter 24a may be an optical energy source and may be positioned in any suitable location to illuminate the touch panel 20. The position of the transmitter 24a may depend on the type of transmitter used or other factors. In the example shown in FIG. 2, the transmitter 24a is provided generally below the touch panel 20 and touch panel surface 21. In some examples, the transmitter 24a may be provided along a periphery of the touch panel 20 or in another location.

An optical fiber (not shown) may be provided to direct the optical energy to suitable location on the touch panel 20. The type of optical energy produced by the transmitter 24a may also vary, for example, depending on the touch screen technology used. In some examples, light emitting diodes (LEDs), lasers, or incandescent or halogen bulbs may be used. The transmitter 24a or 24b may include a single light source or a plurality of light sources.

The receiver 26a may be a charge-coupled device (CCD), an indium gallium arsenide (InGaAs) semiconductor device, a lead sulfide (PbS) detector element, or some other suitable device and may be positioned in any suitable location to receive optical energy reflected by the touch of a user on the touch panel 20.

The position of the receiver 26a may depend on the type of receiver used or other factors. Generally, the receiver may be positioned in any suitable location to receive energy reflected from the user. In the example shown, the receiver 26a may be provided generally below the transmitter 24a. Such position may be used, for example, with frustrated total internal reflectance touch screen technology. In alternative examples, the receiver 26a may be positioned along a periphery of the touch panel or in other locations, such as separate from the touch-sensitive device.

In some examples, the touch screen component 12 may not include a display screen 22. In general, the touch screen component 12 may recognize a touch event, and the processor 28a may interpret the touch and thereafter perform an action, such as determination of biometric information or of touch position, based on the touch event.

Figure 2B:
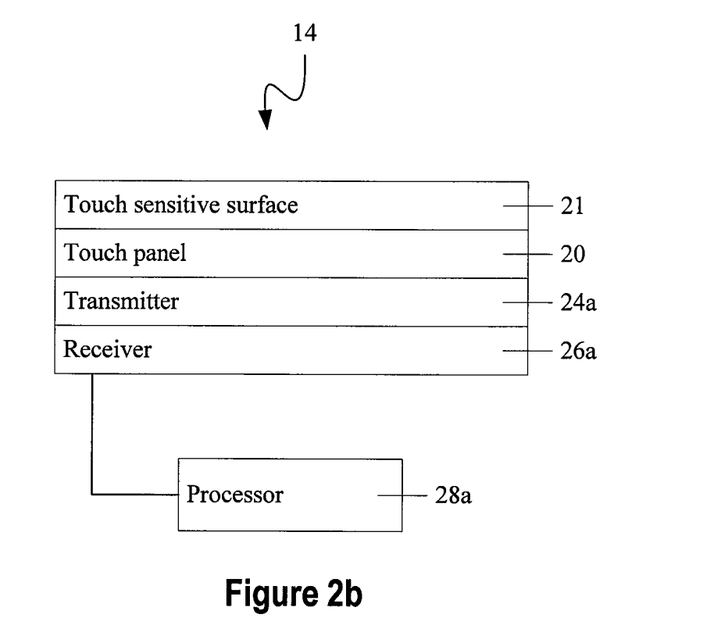
FIG. 2b depicts a spectroscopic component according to certain examples of the present disclosure.
Figure 3:
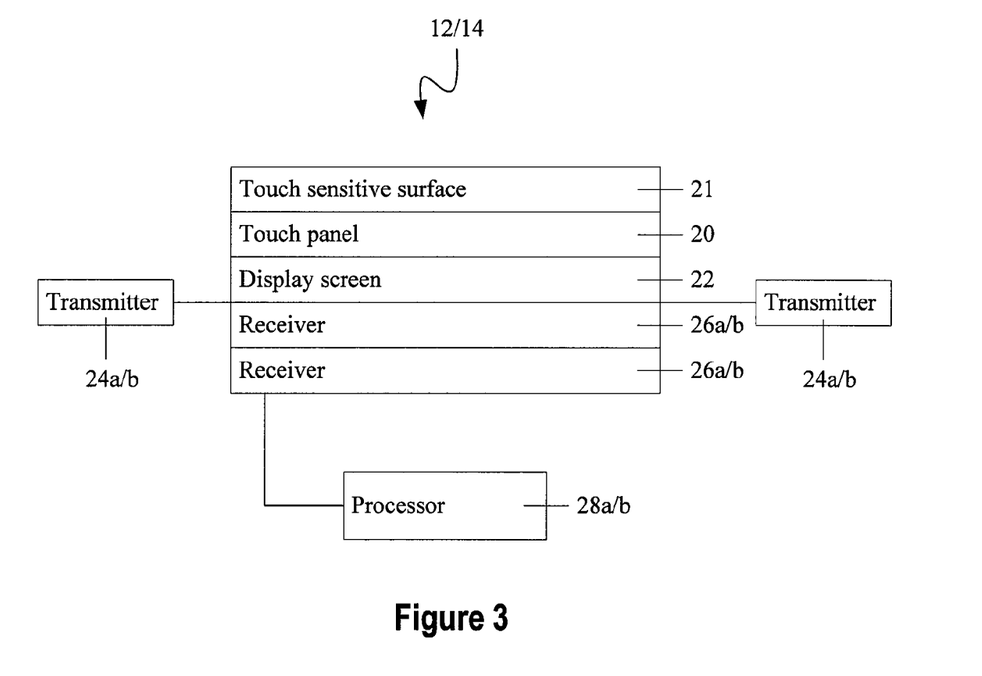
FIG. 3 depicts a touch-sensitive device comprising integrated touch screen and spectroscopic components according to certain examples of the present disclosure.

FIG. 2b depicts a spectroscopic component 14 according to certain examples of the present disclosure. As shown in FIG. 2b, the spectroscopy component 14 may include a touch panel 20 and touch sensitive surface 21 (both of which may be common to the spectroscopic component 14 and the touch screen component 12), a transmitter 24b, a receiver 26b, and a processor 28b. As shown in FIGS. 2 and 3, in some examples, separate transmitters, receivers, and/or processor may be provided for each of the touch screen component 12 and the spectroscopic component 14. FIGS. 2 and 3 illustrate separate transmitters, receivers, and processors (24a and 24b, 26a and 26b, and 28a and 28b, respectively).

The processor 28b of the spectroscopic component 14 may perform an analysis based on data from the sensor to provide biometric information. The transmitter 24b of the spectroscopic component have like characteristics to the transmitter of the touch screen component and discussion of the transmitter 24a is intended to apply also to the transmitter 24b. Accordingly, the transmitter may comprise, for example, an infrared (IR) transmitter for transmitting IR radiation. Correspondingly, the receiver 26b may comprise an IR receiver for receiving IR radiation reflected by a finger or other object in proximity to the panel.

Like the transmitter 24a of the touch screen component, the transmitter 24b may be an optical energy source and may be positioned in any suitable location to illuminate the touch panel 20. In the example shown in FIG. 3, the transmitter 24b is provided generally below the touch panel 20 and touch panel surface 21. In some examples, the transmitter 24b may be provided along a periphery of the touch panel 20 or in another location.

The receiver 26b of the spectroscopic component have like characteristics to the receiver of the touch screen component and discussion of the receiver 26a is intended to apply also to the receiver 26b. Accordingly, the receiver 26b may be a charge-coupled device (CCD), an indium gallium arsenide (InGaAs) semiconductor device, a lead sulfide (PbS) detector element, or some other suitable device and may be positioned in any suitable location to receive optical energy reflected by the touch of a user on the touch panel 20.

FIG. 3 depicts a touch-sensitive device comprising integrated touch screen and spectroscopic components 12/14 according to certain examples of the present disclosure. As shown, the device may include a touch panel 20, a touch-sensitive surface 21, a display screen 22, one or more common transmitters 24a/b, one or more common receivers (or sensors) 26a/b, and a processor 28a.

Accordingly, in some examples, a single transmitter, a single receiver, and a single processor may be provided and may be common to the touch screen component 12 of FIG. 2a and the spectroscopic component 14 of FIG. 2b. A shared single transmitter, receiver, or processor may be referred to as a common transmitter 24*a/b*, a common receiver 26*a/b*, or a common processor 28*a/b*. Accordingly, if one or more of the transmitter, receiver, and processor is common to the touch screen component 12 and the spectroscopy component 14, the system may comprise an integrated touch sensitive and spectroscopy component.

In the example of FIG. 3, two common transmitters 24*a/b* are provided along a periphery of the touch panel 20. These transmitters may be arranged to emit optical energy at different wavelengths. For example, one common transmitter may be used for biometric identification and another common transmitter may be used for analyte (such as blood glucose) measurement.

In the example of a common transmitter 24*a/b* for use as a transmitter 24*a* for detecting optical energy for determining touch location and a transmitter 24*b* for detecting optical energy for determining biometric information by the touch. The optical energy emitted by the common transmitter 24*a/b* may have a wavelength that is absorbed differently based upon analyte concentration in the blood. In the case of near-infrared spectroscopy, the optical energy emitted by the common transmitter 24*a/b* may be in the near infrared range (approximately 800 nm to approximately 1400 nm). In alternative examples, the optical energy may be in the range of 680 nm to 2500 nm). Further, other ranges in the light spectrum may be used. The wavelength used may be selected based on the analyte of interest to be detected in the blood of a user.

The common receiver 26*a/b* may be configured such that a sample of the reflected optical energy (or signal) may be sampled with a first receiver (such as a single CCD) to determine a location of touch and the remaining reflected optical energy (or signal) may be routed to a second receiver for spectral analysis. As shown, in some examples, multiple receivers may be provided, for example multiple common receivers 26*a*/26*b* for receiving reflected optical energy at a different wavelengths. Alternatively, multiple receivers 26*a* and/or multiple receivers 26*b* may be provided. Different biometric information may be gathered from optical energy at different wavelengths. It is to be appreciated that in various examples, filters (not shown) may be provided, for example, between the touch panel 20 and the receiver to filter out optical energy having wavelengths in a non-desired spectrum.

Referring to touch sensitive devices from any of the examples discussed above, light emitted from the transmitter 24*a*, 24*b*, or 24*a/b* may be directed to the surface of the touch panel 20. When a user contacts the surface of the touch panel 20, light emitted from the transmitter may in part be reflected from the user's skin. Generally, the amount or other property of light reflected may depend on concentrations of analytes in the blood of the user. For example, in those regions of the spectrum in which the user's skin absorbs optical energy or light, some portion of the light may not be reflected back. It is these regions of absorbance that may provide information for quantification of, for example, analyte level. The receiver 26*a*, 26*b*, or 26*a/b* thus may sense light reflected back as a result of touch by the user. Dispersive elements such as prisms or gratings (not shown) may be provided to pass the reflected light to the receiver. Generally, the receiver is configured to receive reflected optical energy at the wavelength transmitted by the transmitter. Thus, if the transmitter transmits optical energy at a first wavelength, the receiver receives optical energy at the first wavelength.

For some analyte measurements, it may be desirable to provide at least two receivers (and in some examples, two transmitters). Specifically, at least two receivers may be provided for simultaneously measuring absorbance of two specific regions in the relevant spectrum: a reference wavelength and a measuring wavelength. The transmitter thus may emit energy at least in the region of the referencing wavelength and the measuring wavelength. An IR absorbance spectra may be generated for any analyte of interest. Generally, such spectra will show that, in certain regions of the IR spectrum, there is a correlation between absorbance and the concentration of that analyte. Further, there typically is a region in which the absorbance is not at all dependent upon the concentration of that analyte. The processor 28*a* or 28*b* thus may use these two regions in the IR spectra as a referencing wavelength and a measuring wavelength, respectively.

The processor may be used to determine location of touch based on the reflected optical energy received by the receiver and the processor may be used to determine biometric information based on the reflected optical energy received by the receiver. In a fully integrated system, a processor may be used to determine location of touch and biometric information based on reflected optical energy received by the receiver. Thus, information, such as a signal, may be transmitted from the receiver to the processor, for example via a bus. The information may be data including an amount of optical energy received at a particular wavelength. The processor may use the information coupled with chemometric, or other algorithms (including multivariate analysis, partial least squares, or other suitable calibration modeling technique) to develop the desired information. The processor may be configured to transmit the developed information to the touch screen display or to other output device and/or may store the developed information in system memory.

When a referencing wavelength and a measuring wavelength are received by the receiver, those wavelength components in the reflected energy may be quantified by the processor to determine the level of a desired analyte, such as glucose.

Figure 4:
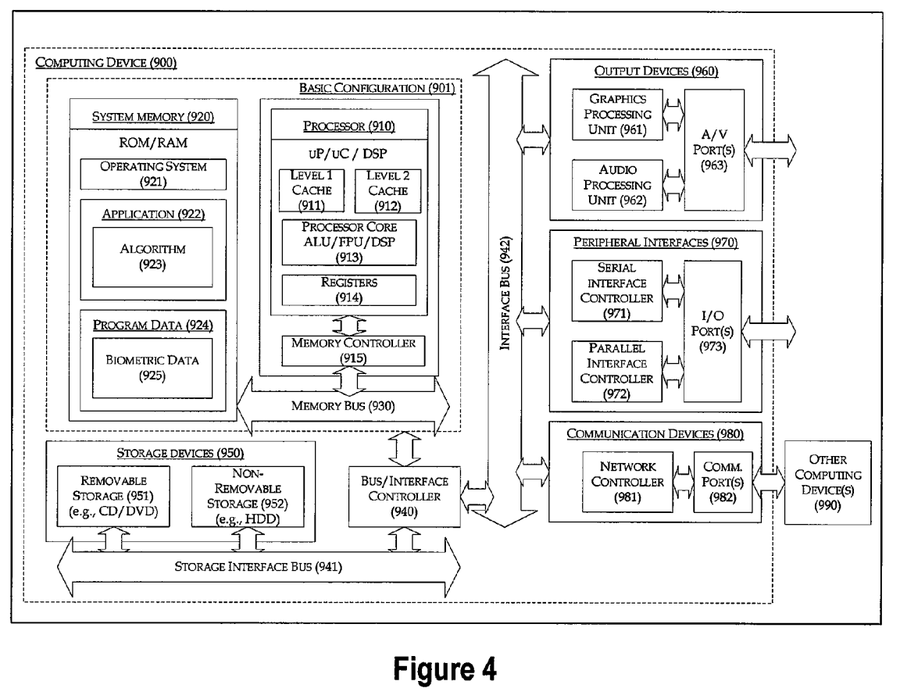
FIG. 4 is a block diagram of a computing device in which a touch sensitive display device may be integrated in order to execute methods for determining biometric information in accordance with the present disclosure.

FIG. 4 is a block diagram of a computing device in which a touch sensitive display device may be integrated in order to execute methods for determining biometric information in accordance with the present disclosure. As shown, the computing device 900 includes an integrated touch-sensitive display device and spectroscopy device that may be used to obtain biometric information via touch. Thus, for example, the system 10 described in relation to FIG. 1 may be integrated within a computing device 900 in accordance with some implementations.

In a very basic configuration 901, the computing device 900 may include one or more processors 910 (such as separate processors 28*a* and 28*b* or a common processor 28*a*/28*b*) and system memory 920. A memory bus 930 may be used for communicating between the processor 910 and the system memory 920.

Depending on the desired configuration, the processor 910 may be of any type including but not limited to a microprocessor ($\mu P$), a microcontroller ($\mu C$), a digital signal processor (DSP), an ARM968 processor, other processor with suitable functionality and capabilities, or any combination thereof. The processor 910 may include one more levels of caching, such as a level one cache 911 and a level two cache 912, a processor core 913, and registers 914. The processor core 913 may include an arithmetic logic unit (ALU), a floating point unit (FPU), a digital signal processing core (DSP Core), or any combination thereof. In alternative implementations, the touchscreen system may have dedicated logic, such as a state machine. A memory controller 915 may also be used with the processor 910, or in some implementations the memory controller 915 may be an internal part of the processor 910. In some embodiments, the touch screen, processor, and peripherals may be integrated into a single application specific integrated circuit (ASIC).

Depending on the desired configuration, the system memory 920 may be of any type including but not limited to volatile memory (such as RAM), non-volatile memory (such as ROM, flash memory, etc.) or any combination thereof. System memory 920 typically includes an operating system 921, one or more applications 922, and program data 924. Application 922 may include an algorithm 923 that is arranged to process information from the spectroscopy device to determine desired biometric information. Program Data 924 may include, for example, biometric data 925 that is useful for correlating information gathered by the spectroscopy device to the appropriate biometric information, for example correlating data to analyte levels. In some examples, application 922 may be arranged to operate with program data 924 on an operating system 921 such that biometric information may be determined. This described basic configuration is illustrated in FIG. 4 by those components within dashed line 901.

The computing device 900 may have additional features or functionality, and additional interfaces to facilitate communications between the basic configuration 901 and any required devices and interfaces. For example, a bus/interface controller 940 may be used to facilitate communications between the basic configuration 901 and one or more data storage devices 950 via a storage interface bus 941. The data storage devices 950 may be removable storage devices 951, non-removable storage devices 952, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Examples of computer storage media may include volatile and nonvolatile, removable and non-removable media implemented in any method or technology for storage of information, such as computer readable instructions, data structures, program modules, or other data.

System memory 920, removable storage 951 and non-removable storage 952 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of device 900.

The computing device 900 may also include an interface bus 942 for facilitating communication from various interface devices (e.g., output interfaces, peripheral interfaces, and communication interfaces) to the basic configuration 901 via the bus/interface controller 940. Examples of output devices 960 include a graphics processing unit 961 and an audio processing unit 962, which may be configured to communicate to various external devices such as a display or speakers via one or more A/V ports 963. Examples of peripheral interfaces 970 include a serial interface controller 971 or a parallel interface controller 972, which may be configured to communicate with external devices such as input devices (e.g., keyboard, mouse, pen, voice input device, touch input device, etc.) or other peripheral devices (e.g., printer, scanner, etc.) via one or more I/O ports 973. An example of a communication device 980 includes a network controller 981, which may be arranged to facilitate communications with one or more other computing devices 990 over a network communication via one or more communication ports 982. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. The computing device 900 may also be implemented as a personal computer including both laptop computer and non-laptop computer configurations. The computing device 900 may also be implemented as an interactive system such as an information kiosk, television, or a gaming device.

Figure 5:
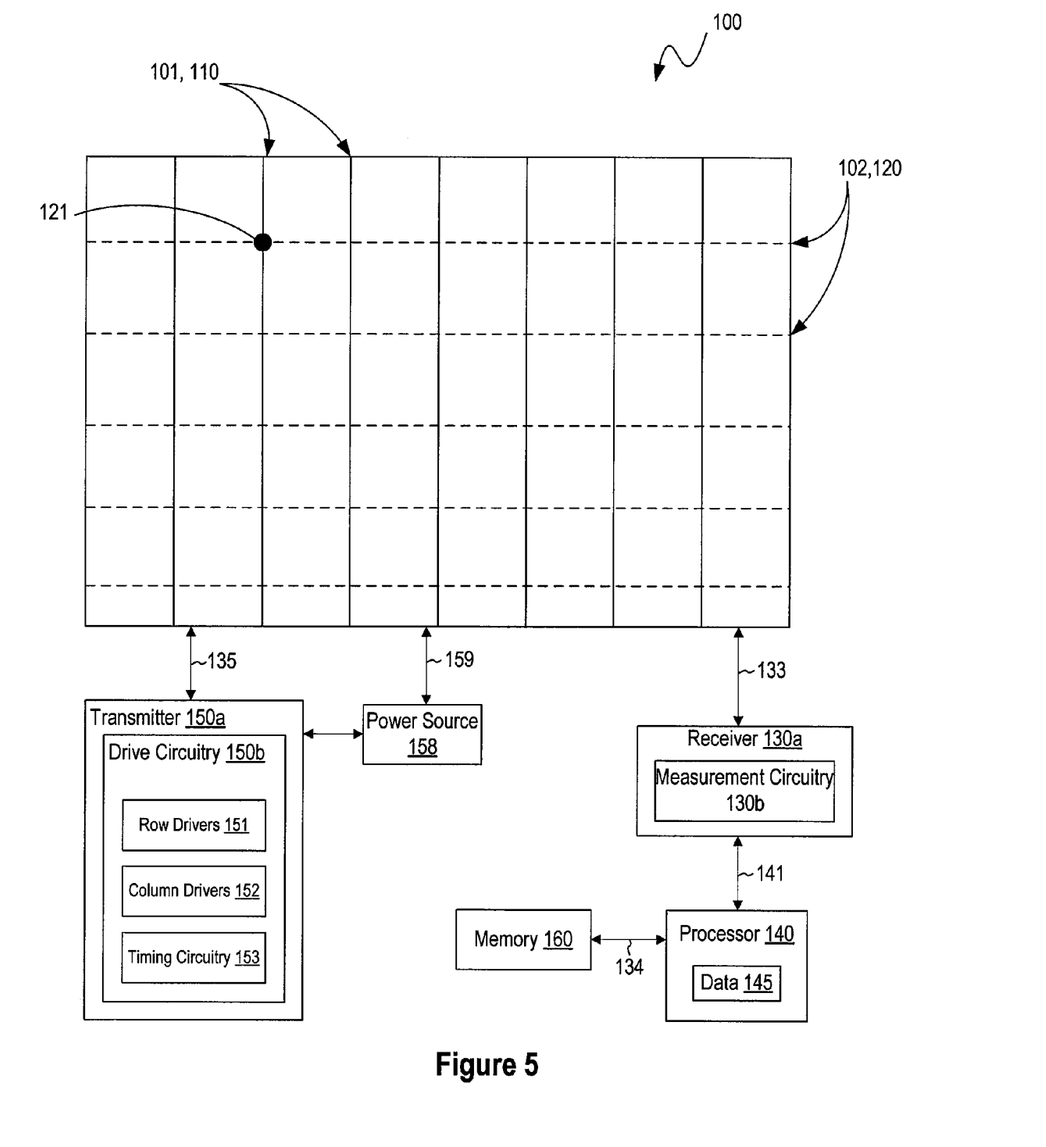
FIG. 5 depicts a cross-sectional view of a touch-sensitive device according to certain examples of the present disclosure.

FIG. 5 depicts a cross-sectional view of a touch-sensitive device according to certain examples of the present disclosure. As described more fully below, the touch-sensitive device 100 may, in some examples, comprise a capacitive sensing medium having a plurality of rows 120 (also referred to as row traces or driving lines) and a plurality of columns 110 or (also referred to as column traces or sensing lines), although other sensing media may alternatively be used. The row and column traces may be formed from a transparent conductive medium, such as Indium Tin Oxide (IT)) or Antimony Tin Oxide (ATO), other transparent and non-transparent materials, such as copper, or other suitable medium. In some examples, the row and column traces may be formed perpendicular to each other, although in other examples, non-orthogonal orientations are possible. In various examples, the rows and columns may be formed on a single side of a substrate, may be formed on opposite sides of a substrate, or may be formed on two separate substrates separated by a dielectric material. In some examples, the dielectric material may be transparent, such as glass, or formed of other materials, such as mylar. An additional dielectric cover layer may be placed over the row or column traces to strengthen the structure and protect the device from damage.

In the specific example of FIG. 5, the touch screen device 100 is configured to serve as both a touch screen and a display, and includes: a first touch-sensitive display layer 101, a second touch-sensitive display layer 102, first layer columns 110, second layer rows 120, nodes 121, a receiver 130a, including measurement circuitry 130b, a processor 140, a transmitter 150a, including drive circuitry 150b, and a memory 160. The drive circuitry 150b may, in some examples, includes row drivers 151, column drivers 152, and timing circuitry 153.

The first touch-sensitive display layer 101 includes a series of columns 110. The second touch-sensitive display layer 102 includes a series of rows 120. The first touch-sensitive layer 101 is disposed over the second touch-sensitive display layer 102. Columns 110 and rows 120 may be formed of one or more conductive layers separated by a series of organic layers. When a voltage is applied to the touch-sensitive display device 100, columns 110 and rows 120 are oppositely charged, and each column 110/row 120 intersection point corresponds to a node 121 of the touch-sensitive display device 100 that may carry a reference signal (e.g., a sine wave reference signal). The node 121 may be illuminated. A node 121 may be considered a type or part of a transistor and/or may be considered a display pixel. The transmitter 150a may be configured to emit an optical energy that is directed to the first and second layers 101, 102.

At node(s) 121 where the display is touched, at least a portion of incident light emitted from the transmitter 150a may be reflected back to the receiver 130a. In some examples, measurement circuitry 130b of the receiver may experience a change as a result of the touch, such as a change in voltage due to a capacitance change in the display. This is because when a finger touches the screen, the finger (i.e., the living body) has stored electrons and exhibits a capacitance. The touch draws a certain amount of the current to the point of contact, which creates a change in voltage, e.g., a voltage drop or increase in capacitance. Thus, touching the display may change the amount of capacitance between the first and second layers 101, 102 from a nominal capacitance value to some other value. In touch screen examples, for each of the nodes 121 and associated measurement circuitry 130 affected by the touch, a processor 140 may be arranged to receive and compares the differences between signals associated with the measurement circuitry 130 affected by the touch to determine the location of the touch on the display.

As previously noted, other types of touch screen technology may be used and location of touch need not be measured based on capacitance. Further, in some examples, location of touch may not be determined and the receiver may merely note that a touch event has occurred and use that information to trigger processor development of biometric information based on reflected optical energy received by the receiver 130a.

In some examples, a power source 158 may be provided as part of the transmitter 150a or separately therefrom. According to some examples, the power source 158 may be coupled to the display via, for example, connection 159 and may be responsible for generating power sufficient to supply optical energy via the transmitter 150a, charge in the display and measurement circuitry at a location associated with at least one of the touch sensitive locations to generate a change in respective associated measurement circuitry indicative of the location of the touch, or other power. The transmitter 150a may be communicatively coupled with the display via connection 135. In some examples, measurement circuitry 130b may be electrically coupled at each node 121 via connection 133. In addition, the processor 140 may be communicatively coupled to receiver 130a generally via connection 141, including, in some examples, to measurement circuitry 130b, the processor 140 may be communicatively coupled to the memory 160 via connection 134.

In examples using capacitive touch technology, at the intersections of the traces, where the traces cross one another, the traces form two electrodes. This is because the traces pass at different layers with respect to one another (e.g., one layer above and one layer below) and do not make direct electrical contact with one another. The intersections may be referred to as "nodes" and may represent pixels of the display. Each intersection of row and column traces may represent a capacitive sensing node. The capacitance between row and column electrodes may appear as a stray capacitance on all columns when the given row is held at DC and as a mutual capacitance Csig when the given row is stimulated with an AC signal. The presence of a finger or other object near or on the panel may be detected by measuring changes to Csig. The columns of the panel may drive one or more analog channels (also referred to as event detection and demodulation circuits). In some examples, each column may be coupled to a dedicated analog channel. In other examples, the columns may be coupleable via an analog switch to a fewer number of analog channels.

The touch screen device may include a processor 140 with data 145 associated with the change in the circuit, the degree or magnitude of sine wave distortion sensed by the circuit, or the change in capacitance sensed by the circuit. The processor may use the data from the shared circuit to determine the circuit(s) experiencing the highest degree of change, and may identify one or more areas of the touch-sensitive display as the location(s) of the touch (e.g., the central force points or the focal points of the touch).

Accordingly, in accordance with some implementations, NIR radiation may be emitted across an array of vertical and horizontal traces, rows 120 and columns 110, using a combined transmitter 150a. A combined receiver 130a may be provided on a receiving end. The receiver 130a may comprise one or more CCDs and may be provided with a dispersive element. It is to be appreciated that, in some examples, the receiver 130a may be a common receiver. Upon detection of a touch event, reflected energy may be communicated from the node 121 to receiver 130a via connection 133. Some portion of the reflected energy (or light) may be sampled and passed to measurement circuitry 130b to determine location of touch using processor 140. The remaining reflected energy (or light) may be passed through the grating and receiver 130a to the processor 140 via connection 141 for analysis. In some examples, a set of optical switches may be used to enhance signal-to-noise ratio (SNR) by passing active traces to the receiver 130a.

In a further examples, the columns 110 and rows 120 may be provided as an array of optical fibers (not shown). Such fibers may be provided beneath a touch screen display (20 of FIG. 2a). The transmitter 150a may be arranged to provide optical energy to the array using a single optical switch, such as a MEMS-based switch, or other suitable switch device. It is to be appreciated that in some examples, the transmitter 150a may be a common transmitter. In the example of a transmitter 150a including a MEMS-based switch, optical energy may be generated at a single point, directed to the fiber that correlates with a user's position, and that fiber may transmit and collect the reflected light. The reflected light may be transmitted to a single receiver 130a. The receiver 130a may generate a signal responsive to the reflected light and transmit the signal to the processor. This example thus may be implemented using a single source of light, a single dispersive element, and a single receiver (such as a set of CCDs).

In some implementations, biometric information may be saved to the system memory 160. The processor (or a separate processor) may be arranged to compare biometric information gathered from the touch with previously stored biometric information. Biometric information may include any information that may be gathered using spectroscopy including information regarding specific chemicals, information regarding biometric identification, or other information. Thus, for example, user history of biometric information, such as glucose levels or cholesterol levels, may be used to make a correlation with respect to whether an individual is following a prescribed diet.

The foregoing describes various examples of touch-sensitive displays having biometric information determination capabilities. Following are specific examples of methods, systems and device utilizing at least some of the above-described features of touch-sensitive displays. These are for illustration only and are not intended to be limiting.

In one example, a device may be provided with a touch-sensitive display and arranged to operate as a glucometer. The device may be configured as a cell phone, a "pen" or other structure. In one example, a touch sensitive "pen" glucometer may be provided with a touch panel wherein a display functionality of touch panel may not be enabled and a secondary output display is provided for showing the glucometer reading. In another example, a touch-sensitive device, configured as a cell phone, pen, or other structure, may include a touch screen and may be arranged for determining blood alcohol content of a user. In another example, a device requiring security may be configured with a touch sensitive component (device or display) that may include a touch screen and may be arranged for determining biometric identification, for example to determine if a user of a computer is an authorized user. In another example, an exercise device may be configured with a touch sensitive component (device or display) that may include a touch screen and may be arranged for determining biometric identification. In some examples, the identification may trigger calling of specific workouts or workout histories.

In accordance with one implementation, a device including a display with at least one touch sensitive location, a transmitter, a receiver, and a processor may be provided. The transmitter emits light in the near infrared region and directs the light to the display. The receiver receives reflected light from a user of the device and transmits the reflected light to the processor. The processor analyzes the transmitted light to determine at least one form of biometric information. In various examples, the biometric information may comprise blood analyte levels, biometric identification information or other.

In accordance with another implementation, a touch sensitive device comprising a touch sensitive component, a spectroscopy component, and a processor may be provided. The touch sensitive component includes a touch panel suitable for application of a touch event. At least one of the touch sensitive component or the spectroscopy component includes a transmitter for transmitting optical energy at a first wavelength and a receiver for receiving reflected optical energy at the first wavelength, wherein the reflected optical energy is reflected pursuant to the touch event. The processor analyzes the reflected optical energy to determine, at least, biometric information based on the reflected optical energy.

In variations of this implementation, the receiver may be common to the touch sensitive component and the spectroscopy component and may comprise a charge-coupled device (CCD). Further, the receiver may be arranged to split the received optical energy into a first portion and a second portion, wherein the first portion may be used by the processor to determine a location of the touch event and the second portion may be used by the processor to determine biometric information.

In further variations, the transmitter may be arranged in common for the touch sensitive component and the spectroscopy component. For example, the transmitter may be arranged to emit optical energy in the range of approximately 800 nanometers to approximately 2500 nanometers, and may comprise one or more light emitting diodes. In some variations, a second receiver may be provided for receiving reflected optical energy at a second wavelength. Differing biometric information may be gathered from optical energy at different wavelengths.

The touch sensitive device may be, for example, a portable hand held device. The biometric information may, in some examples, relate to glucose level of the user or to biometric identification information.

The touch sensitive device may further include a display and the display may be viewed through the touch sensitive surface. The touch sensitive surface may be infrared transparent. The processor may be configured to transmit the determined biometric information to the display, where the display may be configured to present the biometric information for viewing.

In some examples, a plurality of transmitters may be provided with two or more of the transmitters emitting light at different wavelengths. In some variations, the wavelengths may be in a range corresponding to sensitivity of an analyte for measurement.

In a further variation, a secondary display may be provided for outputting the determined biometric information.

Figure 6A:
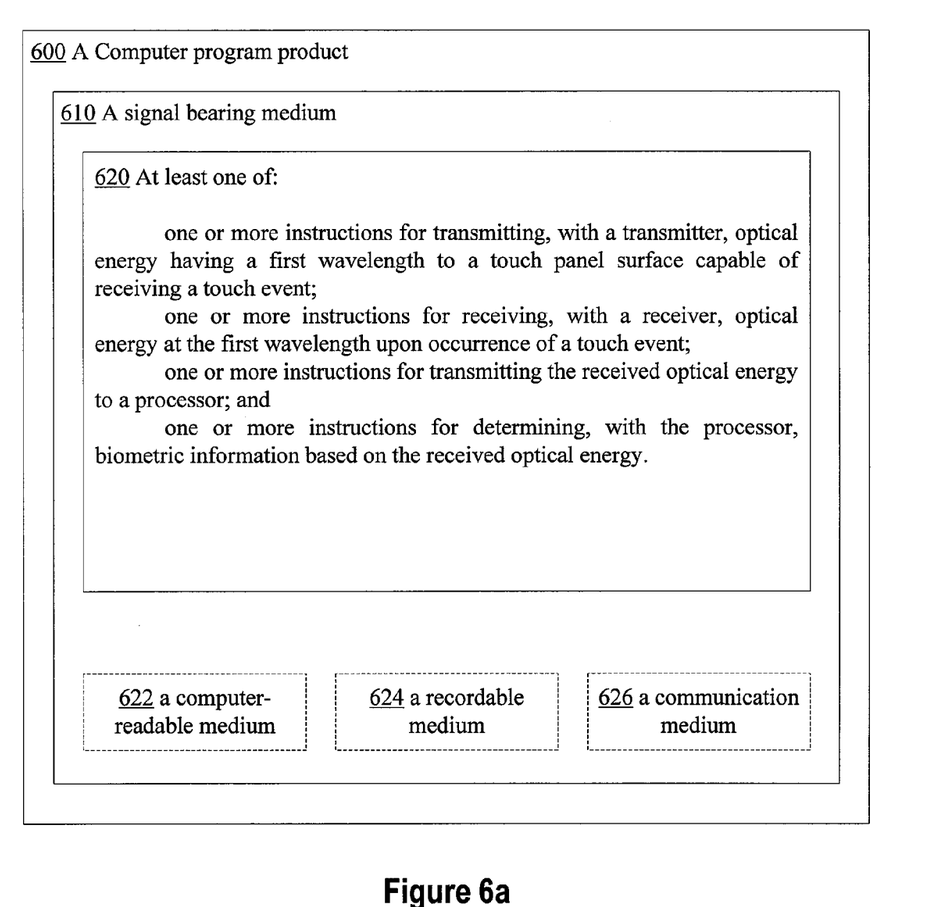
FIG. 6a is a diagram of a system suitable for integrating with touch-sensitive devices in accordance with certain examples of the present disclosure.

FIG. 6A is a diagram of a system suitable for integrating with touch-sensitive devices in accordance with certain examples of the present disclosure. A computer program product 600 may be implemented in computing device 500 for sensing a touch event and determining biometric information of a user and, in some examples, location of the touch event. The computer program product 600 includes a signal bearing medium 610 configured to execute one or more instructions 620. The signal bearing medium 610 may be configured as a computer-readable medium 622, a recordable medium 624 and/or a communications medium 626. The one or more instructions 620 include instructions for transmitting, with a transmitter, optical energy having a first wavelength to a touch panel capable of receiving a touch event, instructions for receiving, with a receiver, optical energy at the first wavelength upon occurrence of a touch event, instructions for transmitting the received optical energy to a processor, and instructions for determining, with the processor, biometric information based on the received optical energy.

Figure 6B:
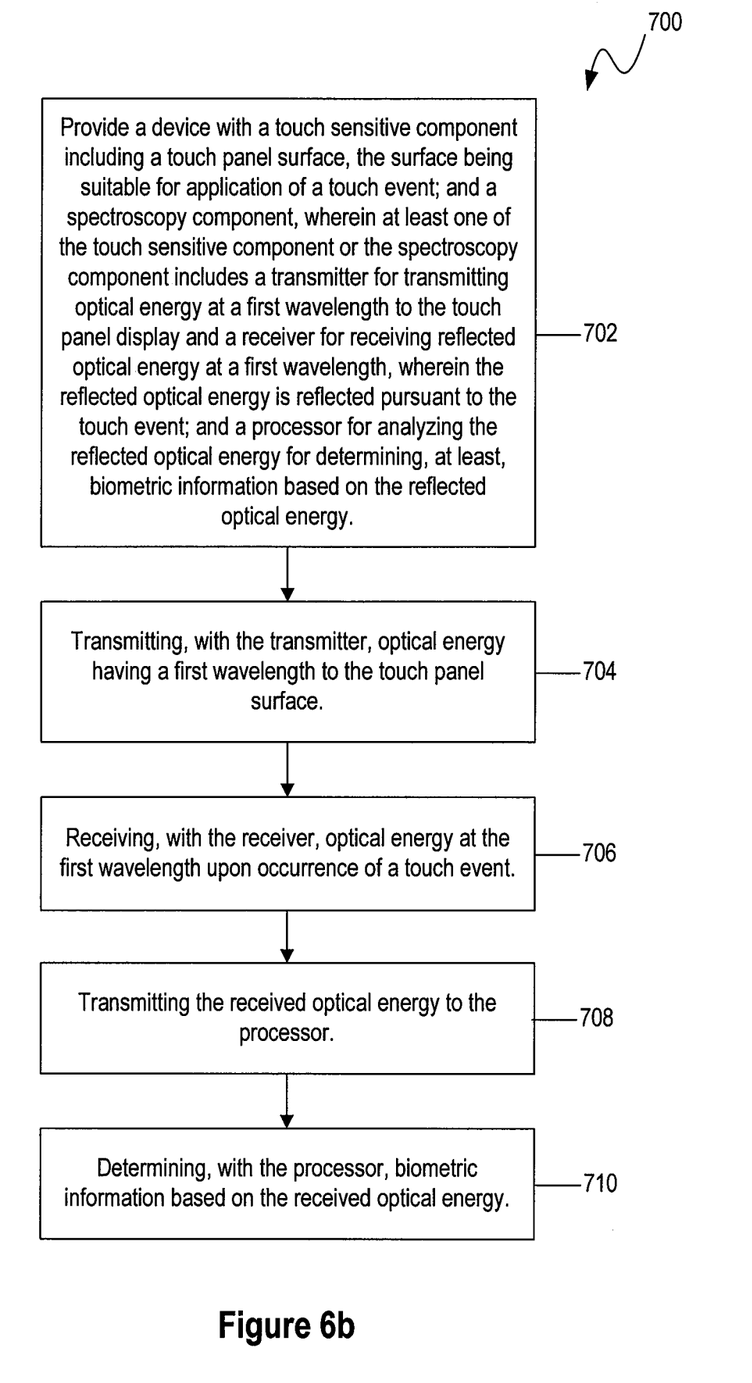
FIG. 6b is a flowchart of a computer-implemented method for sensing a touch on a touch-sensitive device and determining biometric information according to certain examples of the present disclosure.

FIG. 6B is a flowchart of a computer-implemented method for sensing a touch on a touch-sensitive device and determining biometric information according to certain examples of the present disclosure. According to FIG. 6B, the illustrated method 700 may include one or more of operations/actions/blocks 702, 704, 706, 708 and 710.

The method may include providing a device with a touch sensitive component including a touch panel, the surface being suitable for application of a touch event; and a spectroscopy component, wherein at least one of the touch sensitive component or the spectroscopy component includes a transmitter for transmitting optical energy at a first wavelength to the touch panel display and a receiver for receiving reflected optical energy at the first wavelength, wherein the reflected optical energy is reflected pursuant to the touch event; and a processor for analyzing the reflected optical energy for determining, at least, biometric information based on the reflected optical energy (block 702). The method may further includes transmitting, with the transmitter, optical energy having a first wavelength to the touch panel (block 704), and receiving, with the receiver, optical energy at the first wavelength upon occurrence of a touch event (block 706). The method may then include transmitting the received optical energy to the processor (block 708) and determining, with the processor, biometric information based on the received optical energy (block 710).

Other implementations may provide touch-sensitive displays or touch screens with measurement circuits that employ one or more of capacitive technology, resistive technology, surface acoustic wave/ultrasonic wave technology, acoustic pulse recognition technology, dispersive signal technology, frustrated total internal reflection technology, infrared technology, and/or strain gauge technology. For example, electric signals associated with sensing a touch on a display employing one or more of the aforementioned technologies may cause electrically coupled LED display and measurement circuit(s) to experience a change, and a processor in association with measurement circuits coupled to each of the LEDs affected may determine the location of the touch and biometric information associated with the user.

According to certain implementations, the device may be operable when one or more portions of the touch screen display are not visibly illuminated. For example, when the portion of the display is not active or not visibly illuminated, optical energy in the NIR region may nevertheless be transmitted to the display surface. A touch to the touch-sensitive display may cause the receiver to receive reflected light and trigger processing by the processor. The processor may be arranged to determine biometric information and, in some examples, location of the touch. Upon determination of biometric information, the device may be visibly illuminated to display the determined information.

The present disclosure is not to be limited in terms of the particular examples described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various examples of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like include the number recited and refer to ranges which may be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A touch sensitive device having spectroscopy components, the touch sensitive device comprising:
   a display;
   a touch panel arranged to generate a signal responsive to a touch, wherein the display is viewable through the touch panel;
   a transmitter operable to transmit optical energy at a first wavelength to the touch panel, the first wavelength being useful for spectroscopically detecting an analyte;
   a receiver operable to receive optical energy reflected responsive to the touch; and
   a processor coupled to the receiver and arranged to analyze the reflected optical energy to determine, responsive to the touch and using spectroscopy, concentration of the analyte in blood determined from the reflected optical energy using chemometric algorithms.

2. The touch sensitive device of claim 1, wherein the receiver comprises a charge-coupled device.

3. The touch sensitive device of claim 1, wherein the touch is initiated by a user, wherein the receiver is operable to split the received optical energy into a first portion and a second portion, and wherein the processor is configured to determine a location of the touch on the touch panel with the first portion and further configured to determine the concentration of the analyte in the blood of the user with the second portion.

4. The touch sensitive device of claim 1, wherein the transmitter is configured to emit optical energy in the range of approximately 800 nanometers to approximately 2500 nanometers.

5. The touch sensitive device of claim 1, wherein the transmitter comprises one or more light emitting diodes.

6. The touch sensitive device of claim 1, wherein the touch sensitive device comprises a portable hand held device.

7. The touch sensitive device of claim 1, wherein the concentration of the analyte in blood is the glucose level of a user creating the touch.

8. The touch sensitive device of claim 1, wherein the processor is configured to transmit the determined concentration of the analyte in blood to the display, where the display is configured for presenting the concentration of the analyte in blood.

9. The touch sensitive device of claim 1, wherein the touch panel is infrared transparent.

10. The touch sensitive device of claim 1, wherein the touch event is initiated by contact of the touch panel with a finger of the user.

11. The touch sensitive device of claim 1, wherein the transmitter is provided along a periphery of the touch panel.

12. The touch sensitive device of claim 1, wherein the transmitter is further configured to emit light at a second wavelength.

13. The touch sensitive device of claim 12, further comprising a second receiver operable to receive reflected optical energy at the second wavelength wherein the processor may analyze additional spectroscopic information from reflected energy at the second wavelength.

14. A method for determining a concentration of an analyte in blood, the method comprising:
transmitting optical energy having a first wavelength to a touch panel of a display, wherein the display is viewable through the touch panel;
receiving optical energy at the first wavelength responsive to a touch event initiated by a user;
using the received optical energy to provide location information about the touch event; and
determining, from the received optical energy using spectroscopy, a concentration of analyte in blood of the user responsive to the touch event.

15. The method of claim 14, wherein transmitting the optical energy illuminates the touch panel.

16. The method of claim 14, wherein the first wavelength is between approximately 900 nm and approximately 2500 nm.

17. The method of claim 14, further comprising generating an infrared absorbance spectra for an analyte of interest, wherein the first wavelength is based on the infrared absorbance spectra.

18. The method of claim 14, wherein determining the concentration of the analyte in blood includes applying chemometric algorithms to the received optical energy.

19. The method of claim 14, further comprising providing a visual display of the determined concentration of the analyte in blood.

20. The method of claim 14, further comprising storing the determined concentration of the analyte in blood.

21. The method of claim 14, further comprising contacting the touch panel with a finger of the user to initiate the touch event.

22. The method of claim 14, wherein the transmitting includes transmitting optical energy from a periphery of the touch panel.

* * * * *

UNITED STATES PATENT AND TRADEMARK OFFICE
CERTIFICATE OF CORRECTION

PATENT NO. : 8,786,575 B2  Page 1 of 1
APPLICATION NO. : 12/467943
DATED : July 22, 2014
INVENTOR(S) : Miller It is certified that error appears in the above-identified patent and that said Letters Patent is hereby corrected as shown below:

On Title Page 2, in Item (56), under "OTHER PUBLICATIONS", in Column 2, Line 5, delete ""Pluse" and insert -- "Pulse --, therefor.

On Title Page 2, in Item (56), under "OTHER PUBLICATIONS", in Column 2, Lines 8-11, delete "Creaghbrown, "How does Pulse Oximetry Work?", http://www.creaghbrown.co.uk/anae/pulsox.htm. Masimo, "Masimo Rainbow SET Pulse CO-Oximetry", http://www.masimo.com/rainbow/about.htm.".

In the Specification:

In Column 3, Line 5, delete "(SNR) ratio," and insert -- ratio (SNR), --, therefor.

In Column 3, Line 51, delete "panel surface" and insert -- sensitive surface --, therefor.

In Column 4, Line 45, delete "panel surface" and insert -- sensitive surface --, therefor.

In Column 8, Line 37, delete "(IT))" and insert -- (ITO) --, therefor.

In Column 14, Line 14, delete "and or" and insert -- and/or --, therefor.

Signed and Sealed this
Eighteenth Day of November, 2014

Michelle K. Lee
*Deputy Director of the United States Patent and Trademark Office*